United States Patent [19]

Kaufmann et al.

[11] Patent Number: 4,917,891
[45] Date of Patent: Apr. 17, 1990

[54] COMPOSITION HAVING EVAPORATIVE OIL-LIKE MATERIAL

[75] Inventors: Peter J. Kaufmann, Raleigh; Charles G. Friedman, Pittsboro, both of N.C.

[73] Assignee: Revlon, Inc., New York, N.Y.

[21] Appl. No.: 33,583

[22] Filed: Apr. 1, 1987

Related U.S. Application Data

[63] Continuation-in-part of Ser. No. 684,635, Dec. 21, 1984, abandoned.

[51] Int. Cl.$^4$ .................. A61K 7/02; A61K 31/695; A61K 9/10; A61K 47/00
[52] U.S. Cl. ........................ 424/401; 514/63; 514/844; 514/845; 514/846; 514/847; 514/848; 514/859; 514/714; 424/63; 424/613; 424/705
[58] Field of Search ............... 424/63, 162, 401, 613, 424/705; 514/63, 844–848, 859, 714

[56] References Cited

U.S. PATENT DOCUMENTS 4,478,853 10/1984 Chaussee .......................... 424/59
4,563,346 1/1986 Deckner .......................... 514/859

OTHER PUBLICATIONS

Harry's Cosmeticology, Seventh Ed., (1982), pp. 307, 121–123.
Strianse, in Cosmetics: Science and Technology, Second Ed., vol. 1, (1972), pp. 186–188, 193, 196–197, 201, 204–205.

Primary Examiner—Jacqueline M. Stone
Attorney, Agent, or Firm—Donald T. Black

[57] ABSTRACT

A composition absent animal, vegetable and mineral oils, which composition has an oil and water emulsion which includes a volatile oil-like material which evaporates while on a wearer after a period of time. The emulsion also includes basically deionized water and emulsifiers. Further, the composition includes additives such as stabilizers, oil absorbers, modifiers, dispersants, humectants and preservatives. The composition can be changed to be a make-up, therapeutic or enhanced moisture lotion composition.

23 Claims, No Drawings

COMPOSITION HAVING EVAPORATIVE OIL-LIKE MATERIAL

RELATED APPLICATION

This is a continuation-in-part application of U.S. patent application Ser. No. 684,635 filed on December 21, 1984 for COMPOSITION HAVING AN EVAPORATIVE OIL-LIKE MATERIAL in the names of Peter J. Kaufmann and Charles Gene Friedman, now abandoned.

BACKGROUND OF THE INVENTION

1. Field of the Invention

The present invention relates to a composition having a volatile oil-like material and, more particularly, to a composition having a volatile oil-like material which evaporates while on a wearer after a period of time.

2. Description of the Related Art

Individuals are becoming more increasingly aware that undesirable skin conditions can be caused or aggravated by oils found in various products including cosmetic products. One of the most common undesirable skin conditions is acne. A comedo is the precursor to the inflamed acneiform lesion which occurs when the comedo ruptures through the follicular wall. An individual comedo represents a sebaceous follicle, which has become clogged when the follicular epithelium undergoes hyperkeratinization. Some oils present in cosmetic and therapeutic products can initiate the follicular hyperkeratinization.

Because of the potential some oils have for producing undesirable skin conditions and, in particular, acne, some cosmetic manufactures have developed so called "oil-free" cosmetic-type products which do not include animal, vegetable or mineral oils. However, these "oil-free" products often contain a synthetic oil which may, nevertheless, cause undesirable skin conditions.

Thus, the problem of undesirable skin conditions, such as acne related to the use of oil containing compositions, has not been completely resolved, even in "oil-free" cosmetic-type products, since an oil of some form remains on the wearer for a relatively long period of time.

SUMMARY OF THE INVENTION

It is an object of the present invention to provide a composition that minimizes the exposure of a wearer to oil or oil-like materials contained in topical compositions applied to the body of the wearer.

It is another object of the present invention to provide a composition that is noncomedogenic.

It is also an object of the present invention to provide a composition which has little potential to cause or aggravate undesirable skin conditions such as acne.

It is a further object of the present invention to provide a composition that is formulated and developed for individuals having oily skin and/or having undesirable skin conditions such as, for example, acne.

It is still a further object of the present invention to provide a composition that is free of animal, vegetable and mineral oils and includes a volatile oil-like material that evaporates on a wearer over a relatively short period of time in order to minimize the exposure of the wearer to oil-like materials in the composition.

It is still a further object of the present invention to provide a composition that is free of animal, vegetable and mineral oils, includes a volatile oil-like material that evaporates over a relatively short period of time while on a wearer, and imparts a pleasing, lubricating feel heretofore not typically found in oil-free products.

It is yet a further object of the present invention to provide a makeup composition that is free of animal, vegetable and mineral oils and includes a volatile, oil-like material that evaporates while on the wearer like the base topical composition as well as certain additives to provide the composition with enhanced make-up properties.

It is yet a further object of the present invention to provide a therapeutic composition that is free of animal, vegetable and mineral oils and includes a volatile, oil-like material that evaporates while on a wearer like the basic topical composition, and further includes an anti-acne agent to provide the composition with enhanced therapeutic properties.

It is yet a further object of the present invention to provide a moisture lotion composition that is free of animal, vegetable and mineral oils and includes a volatile, oil-like material that evaporates while on a wearer along with the basic topical composition, and further includes a water soluble moisture binding material to provide the composition with enhanced moisture lotion properties.

These and other objects are provided for by the present invention which, in brief summary, includes a basic topical composition which is free of animal, vegetable and mineral oils, and further includes a volatile, oil-like material which evaporates over a relatively short period of time while on a wearer. Accordingly, after that relatively short period of time that the composition is on the wearer, the composition has substantially less oil than when originally applied and is essentially oil-free so that the potential for developing undesirable skin conditions is significantly reduced.

BRIEF DESCRIPTION OF THE PREFERRED EMBODIMENTS

The present invention provides a composition having an oil and water emulsion, preferably an oil in water emulsion, which includes a volatile oil-like material. The composition may, in a preferred embodiment, also include additives, such as, for example, stabilizers, oil absorbers, modifiers, humectants, preservatives, and may include minor amount of other additives such as acne agents and colorants.

Besides the volatile oil-like material, the emulsion also includes as basic ingredients deionized water and emulsifiers. The volatile oil-like material has, as a principal characteristic, the ability to evaporate in a relatively short period of time, i.e., two or three hours, after application on the wearer. The evaporation is due to the nature of the volatile oil-like material and its response to the normal body temperature of the wearer, which temperature is approximately 37° C. A further characteristic of the volatile oil-like material is that the material imparts a pleasing and lubricating feel on the skin of the wearer.

The volatile oil-like material is a form of a volatile silicone fluid, and is not an animal, vegetable or mineral oil. The volatile silicone fluid may be a cyclic or straight chain fluid, however, a cyclic volatile silicone fluid is recommended since such silicone fluid has the preferred evaporation rate. A preferred cyclic volatile silicone fluid is polydimethycyclosiloxane, which has the chemical structure of 2,4,6,8,10-decamethylcyclopentasiloxane as set forth below:

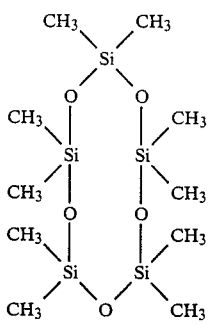

One type of such fluid is sold by Dow Corning under the trade name Dow Corning 345.

Other preferred cyclic volatile silicone fluids which may be used in the composition of the present invention include 2,4,6,8,-octamethylcyclohexasiloxane.

A preferred straight chain volatile silicone fluid is a polyalkyldisiloxane such as hexamethyldisiloxane which has the following chemical structure:

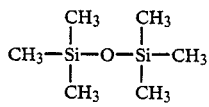

As stated above, the emulsion includes water as the vehicle for the emulsion. The emulsion also includes emulsifiers which may be classified as primary and secondary type emulsifiers. The primary emulsifiers, also known as first or base emulsifiers, may be made alone or from a mixture of polyoxyethylene alkane ethers, polyoxyethylene alkane esters, a combination of polyoxyethylene sorbitan esters, and the reaction products of organic bases and acids.

A preferred primary emulsifier is polyoxyethylene alkane ether, which has from 2 to 20 moles of ethylene oxide in reaction with from 12 to 18 carbon atoms of straight and branched chain alkanols. The preferred combination is:

30% of polyoxyethylene (2 moles) stearyl ether (Steareth-2)
70% of polyoxyethylene (20 moles) stearly ether (Steareth-20)

A hydrophilic/lipophilic balance value of 12.2 should be used in order to achieve the best results as an emulsion.

Another preferred primary emulsifier is a polyoxyethylene alkane ester which has from 2 to 100 moles of ethylene oxide in reaction with from 12 to 18 carbon atoms of straight and branched chain alkyl acids to provide reaction products such as mono, di or tri esters. The preferred combination for this primary emulsifier is:

30% of polyoxyethylene (2 moles) stearate
70% of polyoxyethylene (40 moles) stearate In the preferred primary emulsifier of polyoxyethylene sorbitan ester, the ester has from 2 to 20 moles of ethylene oxide which react with a chemical molecule known as sorbitan and from 12 to 18 carbon atoms of straight and branched chain alkyl acids to provide reaction products such as mono, di or tri esters. The preferred combination for this primary emulsifier is:

25% of sorbitan mono stearate
75% of polyoxyethylene (20 moles) sorbitan monostearate In the primary emulsifier derived from the reaction products of organic bases and acids, the bases are, preferably, selected from a group consisting of mono, di or triethanolamine, mono, di or triisopropanolamine, and the acids are, preferably, selected from a group comprised of lauric, myristic, palmitic, stearic, oleic, linoleic, linolenic and lanolin fatty acids. A preferred combination for this primary emulsifier is:

approximately 28% of triethanolamine
approximately 72% of stearic acid

In the basic topical composition, a secondary emulsifier, also known as a secondary or stabilizing emulsifier, is provided to stabilize and modify the emulsion. A suggested secondary emulsifier is a 24 mole ethylene oxide derivative of cholesterol, commonly referred to as ethoxylated cholesterol. This emulsifier, in addition to its basic role as an emulsifier, has been found to improve the ability of the emulsion to maintain its stable viscosity over periods of time.

As stated above the basic topical composition of the present invention may also include, in a preferred embodiment, one or more additives such as, for example, a stabilizer system, oil absorbers, modifiers for enhancing feel and texture of the resultant composition, humectants, preservatives, as well as minor amounts of other additives.

A stabilizer system is used in the topical composition to provide emulsion stability. Such stabilizer system serve to stabilize the composition by inhibiting the agglomeration and settling of the dispersed particles. The stabilizers which form such stabilizer system are water dispersible, preferably in the form of a gum. Examples of such water dispersible gums which may be used include magnesium aluminum silicate, xanthan gum, and sodium carboxy methyl cellulose. Other gums which can be used include hydroxyethyl cellulose, guar gum, sodium magnesium silicate, hectorite, acrylic acid polymer, acacia gum and gum tragacanth. The stabilizer system may include one or a combination of such gums.

A preferred stabilizer system comprises the following mixture:

| | |
|---|---|
| magnesium aluminum silicate | 72% . |
| xanthan gum | 14% |
| sodium carboxy methyl cellulose | 14% |

Oil absorbers are provided to absorb the natural oils found on the skin of a human. The oil absorbers used in the basic topical composition of the present invention do not themselves contain any oily material. Oil absorbers which have the desired characteristics include bentonite, calcium silicate, magnesium silicate, talc, kaolin, zinc oxide, zinc stearate, magnesium carbonate, magnesium trisilicate, silica, starch, calcium carbonate, lithium stearate, oat flour and Fuller's earth.

A modifier is further provided for the purpose of providing enhanced feel and texture to the resultant composition. The modifier used in the basic topical composition of the present invention preferably includes organoleptic and texture modifiers. Examples of such modifiers include myristyl alcohol, cetyl alcohol, stearyl alcohol, arachidonic alcohol. Such modifiers provide enhanced feel and texture to the composition by increasing the viscosity of the emulsion and providing additional structure to the internal phase, resulting in a richer feeling product.

In a particularly preferred embodiment, a modifier blend is prepared by carefully blending solid fatty alcohols having 14 to 18 carbon atoms, such as cetyl, myristyl and stearyl alcohols. This preferred modifier blend includes a 1:1 ratio of cetyl alcohol (1-hexadecanol) and stearyl alcohol (1-octadecanol). Such a blend has proven particularly effective in providing enhanced feel and texture properties and as well as in stabilizing the composition.

The humectants in the basic topical composition are provided to retain moisture on the surface of the skin of a human. The humectants are polyols or polyhydric alcohols, such as glycerin, sorbitol, 1-3 butylene glycol and propylene glycol, and are water soluble moisture binding materials.

The preservatives in the basic topical composition act to preserve the composition, and may be parabens such as methyl para-hydroxy benzoate (methylparaben), propyl-para-hydroxy benzoate (propylparaben) or imidazolidinyl urea. The amount, calculated by weight of preservatives in the basic topical composition, is from about 0.1% to about 0.8% and, most preferably, between about 0.4% and about 0.8%.

The formula for the base topical composition formulated in accordance with the present invention is:

| TYPE OF INGREDIENT | RANGE BY % WGT | SUGGESTED MATERIAL |
| --- | --- | --- |
| Volatile Oil-Like Materials | 0.5–50.0 | Volatile Silicone Fluid |
| Vehicle | 20–90 | Deionized Water |
| Primary Emulsifiers | 0.2–15.0 | Steareth 2 and Steareth 20 |
| Secondary Emulsifiers | 0.10–2.0 | Ethoxylated Cholesterol |
| Stabilizers | 0–4.50 | Water dispersible gums |
| Oil Absorbers | 0.5–10.0 | Kaolin |
| Modifiers | 0.2–10.0 | Solid Fatty Alcohols |
| Humectants | 1.0–20.0 | Glycerin |
| Preservatives | 0.1–0.8 | Parabens |

Particular preferred results have been obtained when the volatile oil-like material is present in an amount between about 5% and about 15% by weight. Similarly, preferred amounts of the primary emulsifiers have been found to be between about 1% and about 5% by weight. Preferred amounts of oil absorbers are between about 0.5% and about 6% by weight of the total composition.

The above basic topical composition, without any further ingredients, can be used as a moisturizer. However, to create a make-up composition, pigments or colorants and dispersants are also added. To create a therapeutic composition or a composition with enhanced therapeutic lotion properties active ingredients are added. Thus the present invention provides for changes in the basic topical composition which changes create new and different compositions.

MAKE-UP COMPOSITION

To enhance the make-up or cosmetic properties of the basic topical composition, both colorants (or pigments) and dispersants may also be added to the basic composition and the proportions or percentage by weight of the other ingredients will change.

Colorants or pigments are added to the basic composition to provide color which is desired in a make-up composition. It is suggested that the pigment be selected from one of the following: shades of iron oxide, or titanium dioxide, or zinc oxide.

Dispersants, which are primarily pigment dispersants and pigment wetting agents, help to reduce surface tension and disperse each particle of the pigment as well as the oil absorbers when dissolved in the aqueous phase. Accordingly, the dispersants increase the length of time the particles will remain in suspension. Examples of such agents include an acetylated ester of an ethoxylated ether of lanolin alcohol (Laneth-10 Acetate) and the sodium salt of polymethacrylic acid (sodium polymethacrylate).

Accordingly, the formula for the make-up composition in accordance with the present invention is:

| TYPE OF INGREDIENT | % WGT. | MATERIAL |
| --- | --- | --- |
| Volatile Oil-Like Materials | 0.5–50.0 | Volatile Silicone Fluid |
| Vehicle | 20–90 | Deionized Water |
| Primary Emulsifiers | 0.2–15.0 | Steareth 2 and Steareth 20 |
| Secondary Emulsifiers | 0.1–2.0 | Ethoxylated Cholesterol |
| Colorants | 1.0–25.0 | Pigments |
| Stabilizers | 0.2–4.5 | Water dispersible gums |
| Oil Absorbers | 0.5–10.0 | Kaolin |
| Modifiers | 0.2–10.0 | Solid Fatty alcohol |
| Dispersants | 0.25–5.75 | Sodium polymethacrylate |
| Humectants | 1.0–20.0 | Glycerin |
| Preservatives | 0.1–0.8 | Parabens |

The following Examples demonstrate particular preferred forms of the present invention for illustrative purposes only. The true scope of the present invention should be limited only by the claims.

EXAMPLE 1

The following Example 1 is an example of a makeup composition of the present invention which will be subsequently referred to in discussing a method of making the make-up composition of the present invention.

| PHASE | INGREDIENT | % BY WGT. | MATERIAL |
| --- | --- | --- | --- |
| A | Vehicle | Q.S. to 100% | Deionized Water |
| B | Dispersant | 0.5 | Sodium Polymethacrylate |
|   | Dispersant | 2.0 | Laneth-10 Acetate |
|   | Secondary Emulsifier | 0.5 | Ethoxylated Cholesterol (24 mole) |
|   | Stabilizer | 0.5 | Magnesium Aluminum Silicate |
|   | Stabilizer | 0.2 | Xanthan Gum |
|   | Stabilizer | 0.2 | Sodium Carboxy Methyl Cellulose |
| C | Humectant | 5.0 | Glycerin |
| D | Oil Absorber | 5.0 | Kaolin |
|   | Colorant | 7.5 | Shades of Iron Oxides |
|   | Oil Absorber | 2.0 | Bentonite |
| E | Volatile Oil-Like Material | 5.0 | 2, 4, 6, 8, 10-decamethylcyclopentasiloxane |
|   | Modifier | 0.75 | Stearyl alcohol |
|   | Modifier | 0.75 | Cetyl alcohol |
|   | Primary | 0.7 | Steareth-20 |

-continued

| PHASE | INGREDIENT | % BY WGT. | MATERIAL |
|---|---|---|---|
| | Emulsifier | 0.3 | Steareth-2 |
| | Preservatives | 0.5 | Paraben |

The method of preparing the make-up or cosmetic composition of Example 1 is as follows: In a first vessel, deionized water of Phase A is metered. The materials of Phase B and the glycerin of Phase C are premixed in a second vessel, Phase B and Phase C mixture is then added to the deionized water Phase A. A high shear mixer, such as an Eppenbach homomixer, then mixes the Phase B and Phase C mixture with Phase A until a smooth composition is formed. Phase D materials are then added. The new overall mixture is then mixed for one-half hour or until homogenous. The overall mixture formed by combining Phases A, B, C and D is then heated to 70° C. The ingredients of Phase E are premixed and heated to 70° C. When both the overall mixture and the mixture of ingredients of Phase E have reached 70° C., the Phase E ingredients mixture is mixed into the overall mixture by a counter-rotational sweep agitation to form another new mixture which includes the ingredients of Phases A, B, C, D and E. This mixture is mixed for one hour and then cooled to 30° C. to form the make-up composition of the present invention.

In Vitro and In Vivo tests have been conducted to determine the rate of evaporation of a volatile silicone fluid. Concerning the In Vivo tests, a composition having a 12.5 percent volatile silicone fluid, namely Dow Corning Fluid 345, was used to determine by the assay method the rate of evaporation from the skin of three separate human subjects or wearers. Specifically, known amounts of the composition having the 12.5 percent volatile silicone fluid concentration where applied to specified areas of skin of the human subjects under controlled environmental conditions. From this test it was determined that after 1½ hours on the skin, less than 0.625 percent silicone remained on all three wearers tested and, after one hour, less than 0.625 percent of the silicone remained on the skin of two of the three wearers. This means that 95 percent or more of the silicone had evaporated from each of the three wearers over a period of 1½ hours and that 95 percent of the silicone had evaporated from two of the three wearers within a one hour period.

Examples 2 through 4 are examples of specific ingredients and their percentage by weight for the make-up composition of the present invention:

EXAMPLE 2

| INGREDIENT | % BY WGT. | MATERIAL |
|---|---|---|
| Volatile Oil-Like Material | 10.0 | 2, 4, 6, 8, 10-decamethylcyclopentasiloxane |
| Vehicle | 62.35 | Deionized Water |
| Primary Emulsifier | 0.7 | Steareth-20 |
| | 0.3 | Steareth-2 |
| Secondary Emulsifier | 0.5 | Ethoxylated Cholesterol |
| Colorant | 7.5 | Shades of Iron Oxides |
| Colorant | 3.0 | Titanium Dioxide |
| Stabilizer | 0.5 | Magnesium Aluminum Silicate |
| Stabilizer | 0.2 | Xanthan Gum |
| Stabilizer | 0.2 | Sodium Carboxy Methyl Cellulose |
| Oil Absorber | 5.0 | Magnesium Carbonate |

-continued

| INGREDIENT | % BY WGT. | MATERIAL |
|---|---|---|
| Modifier | 2.0 | Myristyl Alcohol |
| Dispersant | 0.25 | Sodium Polymethacrylate |
| Dispersant | 2.0 | Laneth-10 Acetate |
| Humectant | 5.0 | Glycerin |
| Preservatives | 0.50 | Parabens |
| | 100.0 | |

EXAMPLE 3

| INGREDIENT | BY WEIGHT | MATERIAL |
|---|---|---|
| Volatile Oil-Like Material | 10.0 | 2, 4, 6, 8, 10-decamethylcyclopentasiloxane |
| Vehicle | 62.1 | Deionized Water |
| Primary Emulsifier | 0.7 | Steareth-20 |
| | 0.3 | Steareth-2 |
| Secondary Emulsifier | 0.5 | Ethoxylated Cholesterol |
| Colorant | 7.5 | Shades of Iron Oxides |
| Colorant | 3.0 | Titanium Dioxide |
| Stabilizer | 0.5 | Magnesium Aluminum Silicate |
| Stabilizer | 0.2 | Xanthan Gum |
| Stabilizer | 0.2 | Sodium Carboxy Methyl Cellulose |
| Oil Absorber | 5.0 | Kaolin |
| Modifier | 1.0 | Stearyl alcohol |
| Modifier | 1.0 | Cetyl alcohol |
| Dispersant | 0.5 | Sodium Methacrylate |
| Dispersant | 2.0 | Laneth-10 Acetate |
| Humectant | 5.0 | Propylene Glycol |
| Preservatives | 0.5 | Parabens |
| | 100.0 | |

EXAMPLE 4

| TYPE OF INGREDIENT | PERCENTAGE BY WEIGHT | MATERIAL |
|---|---|---|
| Volatile Oil-Like Material | 5.0 | Hexamethyldisiloxane |
| Vehicle | 67.15 | Deionized Water |
| Primary Emulsifier | 0.7 | Steareth-20 |
| | 0.3 | Steareth-2 |
| Secondary Emulsifier | 0.5 | Ethoxylated Cholesterol |
| Colorant | 7.5 | Shades of Iron Oxides |
| Colorant | 3.0 | Titanium Dioxide |
| Stabilizer | 0.5 | Magnesium Aluminum Silicate |
| Stabilizer | 0.2 | Xanthan Gum |
| Stabilizer | 0.2 | Sodium Carboxy Methyl Cellulose |
| Oil Absorber | 5.0 | Bentonite |
| Oil Absorber | 0.2 | Talc |
| Modifier | 1.0 | Stearyl alcohol |
| Modifier | 1.0 | Cetyl Alcohol |
| Dispersant | 0.25 | Sodium Polymethacrylate |
| Dispersant | 2.0 | Laneth-10 Acetate |
| Humectant | 5.0 | Sorbitol |
| Preservatives | 0.5 | Parabens |
| | 100.0 | |

THERAPEUTIC COMPOSITION

Many women desire a therapeutic composition which will treat or improve their acne condition while concealing it cosmetically. Therefore the basic topical composition of the present invention is changed to enhance its therapeutic, i.e., acne treating, properties, and thus become a therapeutic composition.

Specifically, the therapeutic composition as in the basic composition, includes an emulsion having a volatile oil-like material such a silicone fluid that evaporates while on the wearer, and does not include animal, vegetable and mineral oils. A preferred amount of the volatile silicone fluid is between about 5% and about 20% by weight of the total composition. However the therapeutic composition also may include different amounts of ingredients than the basic topical composition and, more importantly, includes an anti-acne agent, such as sulfur or benzoyl peroxide, which is not in the basic topical composition. The sulfur or benzoyl peroxide is included in the therapeutic composition in specific amounts. In particular, the sulfur or benzoyl peroxide can be 1 to 10 percent by weight of the total therapeutic composition; however, it is suggested that for better therapeutic results, the sulfur or benzoyl peroxide should comprise 2.5 to 10 percent by weight of the total therapeutic composition.

It should be noted that dispersants act to disperse the active ingredients such as the anti-acne agents.

The following are four examples of the acne treating cosmetic composition of the present invention in which the anti-acne agent which forms a part of the composition is combined with an emulsion containing volatile silicone fluid.

EXAMPLE 5

| INGREDIENT | % BY WGT. | MATERIAL |
|---|---|---|
| Volatile Oil-Like Material | 10.0 | 2, 4, 6, 8, 10-decamethyl-cyclopentasiloxane |
| Vehicle | 67.08 | Deionized Water |
| Primary Emulsifier | 0.7 | Steareth-20 |
|  | 0.3 | Steareth-2 |
| Secondary Emulsifier | 0.5 | Ethoxylated Cholesterol |
| Stabilizer | 0.8 | Magnesium Aluminum Silicate |
| Stabilizer | 0.2 | Xanthan Gum |
| Oil Absorber | 3.0 | Kaolin |
| Modifier | 1.5 | Stearyl alcohol |
| Modifier | 1.5 | Cetyl alcohol |
| Dispersant | 0.25 | Sodium Polymethacrylate |
| Dispersant | 2.0 | Laneth-10 Acetate |
| Humectant | 5.0 | Propylene Glycol |
| Preservatives | 0.50 | Parabens |
| Anti-Acne Agent | 6.67 | Sulfur (colloidal form) |
|  | 100.0 |  |

EXAMPLE 6

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 57.58 | Deionized Water |
| Primary Emulsifier | 0.7 | Steareth-20 |
|  | 0.3 | Steareth-2 |
| Secondary Emulsifier | 0.5 | Ethoxylated Cholesterol |
| Colorant | 7.5 | Shades of Iron Oxide |
| Colorant | 2.0 | Titanium Dioxide |
| Stabilizer | 0.8 | Magnesium Aluminum Silicate |
| Stabilizer | 0.2 | Xanthan Gum |
| Oil Absorber | 3.0 | Kaolin |
| Modifier | 1.5 | Stearyl alcohol |
| Modifier | 1.5 | Cetyl alcohol |
| Dispersant | 0.25 | Sodium Polymethacrylate |
| Dispersant | 2.0 | Laneth-10 Acetate |
| Humectant | 5.0 | Propylene Glycol |
| Preservatives | 0.5 | Parabens |
| Anti-Acne Agent | 6.67 | Sulfur (precipitated form) |

-continued

| INGREDIENT | % BY WGT. | MATERIAL |
|---|---|---|
|  | 100.0 |  |

EXAMPLE 7

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 68.75 | Deionized Water |
| Primary Emulsifier | 0.7 | Steareth-20 |
|  | 0.3 | Steareth-2 |
| Secondary Emulsifier | 0.5 | Ethoxylated Cholesterol |
| Stabilizer | 0.8 | Magnesium Aluminum Silicate |
| Stabilizer | 0.2 | Xanthan Gum |
| Oil Absorber | 3.0 | Kaolin |
| Modifier | 1.5 | Stearyl alcohol |
| Modifier | 1.5 | Cetyl alcohol |
| Dispersant | 0.25 | Sodium Polymethacrylate |
| Dispersant | 2.0 | Laneth-10 Acetate |
| Humectant | 5.0 | Propylene Glycol |
| Preservatives | 0.5 | Parabens |
| Anti-Acne Agent | 5.0 | Benzoyl Peroxide |
|  | 100.0 |  |

EXAMPLE 8

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 59.25 | Deionized Water |
| Primary Emulsifier | 0.7 | Steareth-20 |
|  | 0.3 | Steareth-2 |
| Secondary Emulsifier | 0.5 | Ethoxylated Cholesterol |
| Colorant | 7.5 | Shades of Iron Oxide |
| Colorant | 2.0 | Titanium Dioxide |
| Stabilizer | 0.8 | Magnesium Aluminum Silicate |
| Stabilizer | 0.2 | Xanthan Gum |
| Oil Absorber | 3.0 | Kaolin |
| Modifier | 1.5 | Stearyl alcohol |
| Modifier | 1.5 | Cetyl alcohol |
| Dispersant | 0.25 | Sodium polymethacrylate |
| Dispersant | 2.0 | Laneth-10 Acetate |
| Humectant | 5.0 | Propylene Glycol |
| Preservatives | 0.5 | Parabens |
| Anti-Acne Agent | 5.0 | Benzoyl Peroxide |
|  | 100.0 |  |

Further, Examples 5 and 6 have sulfur as the anti-acne agent, while Examples 7 and 8 have benzoyl peroxide as the anti-acne agent. In Example 5 the sulfur is in a colloidal form which is a more finely dispersible grade of sulfur than the precipitated sulfur of Example 6.

Further, Examples 6 and 8 include colorants, whereas Examples 5 and 7 do not include colorants. Due to the lack of colorants, the compositions of Examples 6 and 8 have a "vanishing" type appearance, whereas the compositions of Examples 5 and 7 have a more "tinted" appearance.

MOISTURE LOTION COMPOSITION

The basic topical composition can be changed to enhance its moisture lotion properties by changing the basic composition to include a water soluble moisture binding material or materials. Specifically, the moisture lotion composition, like the therapeutic composition, includes the emulsion having a volatile oil-like fluid that evaporates while on the wearer as in the basic composition. However, the enhanced moisture lotion composition also includes from 1 to 20 percent by weight of water soluble moisture binding material such as lactic acid, sodium lactate, urea and sodium pyrrolidone carboxylate (Sodium PCA) not found in either the basic, the make-up or the therapeutic compositions.

The water soluble moisture binding material has the property of further assisting in the retention of water on the skin of the wearer. In addition, the binding material does not feel sticky thereby maintaining a moist, lotion-like feel. Further the moisture lotion composition generally includes additional additives, such as buffers and skin protectants, to add greater moisturizing properties to the basic composition. Examples 9 through 11 are examples of the moisture lotion composition through the above range of water soluble moisture binding materials.

EXAMPLE 9

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 67.9 | Deionized Water |
| Primary Emulsifier | 0.7 | Steareth-20 |
|  | 0.3 | Steareth-2 |
| Stabilizer | 0.25 | Xanthan Gum |
| Stabilizer | 0.75 | Magnesium aluminum silicate |
| Oil Absorber | 1.00 | Talc |
| Oil Absorber | 1.00 | Kaolin |
| Modifier | 1.75 | Stearyl alcohol |
| Modifier | 1.75 | Cetyl alcohol |
| Humectant | 7.5 | Glycerin |
| Humectant | 5.0 | Propylene Glycol |
| Preservative | 0.3 | Methylparaben |
| Preservative | 0.1 | Propylparaben |
| Preservative | 0.3 | Imidazolidinyl Urea |
| Water Soluble Moisture Binding Material | 1.0 | Sodium PCA |
| Other Additive (ph buffer) | 0.15 | Citric Acid |
| Other Additive (ph buffer) | 0.15 | Sodium Citrate |
| Other Additive (skin protectant) | 0.1 | Allantoin |
|  | 100.00 |  |

EXAMPLE 10

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 58.9 | Deionized Water |
| Primary Emulsifier | 0.7 | Steareth-20 |
|  | 0.3 | Steareth-2 |
| Stabilizer | 0.75 | Magnesium Aluminum Silicate |
| Stabilizer | 0.25 | Xanthan Gum |
| Oil Absorber | 1.0 | Talc |
| Oil Absorber | 1.0 | Kaolin |
| Modifier | 1.75 | Stearyl alcohol |
| Modifier | 1.75 | Cetyl alcohol |
| Humectant | 7.5 | Glycerin |
| Humectant | 5.0 | Propylene Glycol |
| Preservative | 0.3 | Methylparaben |
| Preservative | 0.1 | Propylparaben |
| Preservative | 0.3 | Imidazolidinyl Urea |
| Water Soluble Moisture Binding Material | 10.0 | Sodium PCA |

-continued

| INGREDIENT | % BY WGT. | MATERIAL |
|---|---|---|
| Other Additive (ph buffer) | 0.15 | Citric Acid |
| Other Additive (ph buffer) | 0.15 | Sodium Citrate |
| Other Additive (skin protectant) | 0.1 | Allantoin |
|  | 100.00 |  |

EXAMPLE 11

| INGREDIENT | % BY WGT. | MATERIAL |
|---|---|---|
| Volatile Oil-Like Material | 10.0 | 2, 4, 6, 8, 10-decamethylcyclo-pentasiloxane |
| Vehicle | 48.90 | Deionized Water |
| Primary Emulsifier | 0.7 | Steareth-20 |
|  | 0.3 | Steareth-2 |
| Stabilizer | 0.75 | Magnesium Aluminum Silicate |
| Stabilizer | 0.25 | Xanthan Gum |
| Oil Absorber | 1.0 | Talc |
| Oil Absorber | 1.0 | Kaolin |
| Modifier | 1.75 | Stearyl alcohol |
| Modifier | 1.75 | Cetyl alcohol |
| Humectant | 7.5 | Glycerin |
| Humectant | 5.0 | Propylene Glycol |
| Preservative | 0.3 | Methylparaben |
| Preservative | 0.1 | Propylparaben |
| Preservative | 0.3 | Imidazolidinyl Urea |
| Water Soluble Moisture Binding Material | 20.0 | Sodium PCA |
| Other Additive (ph buffer) | 0.15 | Citric Acid |
| Other Additive (ph buffer) | 0.15 | Sodium Citrate |
| Other Additive (skin protectant) | 0.1 | Allantoin |
|  | 100.0 |  |

EXAMPLE 12

In order to demonstrate the impact of varying the amount of the volatile oil-like material in the composition, varying amounts of silicone were added to the base composition with the following results:

| COMPOSITION | RESULTS |
|---|---|
| Base + 5% silicone | Viscosity: high, creamlike (45,000 centipoise) Stability: good Consumer Panel: sticky, did not absorb well, not preferred |
| Base + 12.5% silicone | Viscosity: high, (75,000 centipoise) Stability: good Consistency: preferred for dispensing Consumer Panel: acceptable application and feel. Preferred formula |
| Base + 20% silicone | Viscosity: highest (150,000 centipoise) Stability: good Consistency: too thick Consumer Panel: acceptable application and feel; slight flaking |
| Base + 30% silicone | Viscosity: high Stability: unstable; inverted rapidly Consumer Panel: not tested due to oiliness and inversion |
| Base + 40% silicone | Viscosity: high; Stability: poor Consumer Panel: not tested |
| Base + 50% silicone | Viscosity: extremely high; difficult to emulsify; emulsion inverted Stability: poor Consumer Panel: not tested |

The above test results showed that the best results were obtained when the silicone was included in the composition in an amount of approximately 12.5%.

EXAMPLE 13

In order to demonstrate the impact of varying the amount of the emulsifier in the composition, varying amounts of the emulsifier were added to the base composition with the following results:

| COMPOSITION | | RESULTS (after 4 weeks at 50'C) |
|---|---|---|
| Base + Steareth 20 | 0.84% | Slight syneresis in voids |
| Steareth 2 | 0.36% | |
| | 1.2% | |
| Base + Steareth 20 | 1.4% | Acceptable stability |
| Steareth 2 | 0.6% | |
| | 2.0% | |
| Base + Steareth 20 | 1.12% | Slight creaming on surface |
| Steareth 2 | 0.48% | |
| | 1.60% | |
| Base + Steareth 20 | 1.68% | Syneresis in voids |
| Steareth 2 | 0.72% | |
| | 2.40% | |
| Base + Steareth 20 | 1.96% | Syneresis in voids |
| Steareth 2 | 0.84% | |
| | 2.80% | |

The above test results indicate that the preferred stability ocurred when the emulsifier was added in an amount equal to approximately 2% of the total composition.

EXAMPLE 14

In order to demonstrate the impact of varying the amount of the oil absorber in the composition, varying amounts of oil absorbers were added to the base composition with the following results:

| COMPOSITION | OBSERVATIONS |
|---|---|
| Base + 5% kaolin | Tacky, balled on application |
| Base + 10% kaolin | Severe balling on application |
| Base + 1.2% kaolin | Satisfactory application |

The above test results indicate that the preferred results were obtained when the kaolin was included in an amount equal to about 1.2% of the composition.

Thus, the base topical composition of the present invention has the desirable qualities and properties of a composition containing an oil, but is formulated to minimize the undesirable and potentially harmful results which occur due to the presence of such oil. In particular, by providing a volatile oil-like material, such as silicone fluid, which essentially evaporates while on the wearer over a period of time, the wearer's exposure to oil is minimized. Thus, a wearer is able to wear a composition that, after evaporation, is oil-free.

The basic composition can be changed to a new composition having enhanced therapeutic properties by adding a specific amount by weight of an anti-acne agent. Likewise, the basic composition can be changed to a new composition having enhanced moisture lotion properties by adding a specific amount by weight of water soluble moisture binding material and, in addition, adding other additives than those found in the basic composition. Furthermore, both of these new compositions still retain the feature that the wearer's exposure to oil is minimal as provided for in the basic composition.

The present invention may, of course, be carried out in other specific ways than those set forth herein without departing from the spirit and essential characteristics of the present invention. The present embodiments are, therefore, to be considered in all respects as illustrative and not restrictive, and to provide for all changes coming within the meaning and equivalency range the appended claims are intended to embrace.

Wherefore, we claim:

1. A noncomedogenic, oil-in-water emulsion composition free of animal, vegetable and mineral oils, the composition including:

an emulsifier system in an amount between about 0.30% and about 17% by weight of the total composition;

at least one oil absorber in an amount up to about 10% by weight of the total composition;

a volatile silicone fluid in an amount between about 0.5% to about 20% by weight of the total composition, said silicone fluid being able to impart an essentially oil-free composition on a wearer after evaporation thereof so that the potential for developing undesirable acne skin conditions is significantly reduced; and water in an amount between about 48% to about 67%, wherein the noncomedogenic emulsion composition is viscous with a viscosity between about 45,000 to about 150,000 centipoise so that the composition is a cream, lotion or ointment.

2. The composition of claim 1, wherein said volatile silicone fluid is selected from the group consisting of hexamethyldisiloxane; 2,4,6,8-octamethylcyclotetrasiloxane; 2,4,6,8,10-decamethylcyclopentasiloxane; and 2,4,6,8,10,12-dodecamethylcyclohexasiloxane.

3. The composition of claim 1, wherein said emulsifier system includes a first emulsifier in an amount between about 0.2% and about 15% by weight of the total composition and a second emulsifier in an amount between about 0.1% and about 2% by weight of the total composition.

4. The composition of claim 3, wherein said first emulsifier is a polyoxyethylene alkane ether selected from the group consisting of:

$$CH_3(CH_2)_xCH_2(OCH_2CH_2)_nOH$$

where x represents from 10 to 16, and N represents from 2 to 20.

5. The composition of claim 3, wherein said second emulsifier is ethoxylated cholesterol.

6. The composition of claim 1, further including at least one additive selected from the group consisting of a stabilizer system, feel and texture modifiers, humectants and preservatives.

7. The composition of claim 6, wherein said composition includes a stabilizer system in an amount up to about 4.5% by weight of the total composition; an oil absorber in an amount up to about 10% by weight of the total composition; a feel and texture modifier in an amount between about 0.2% and about 10% by weight of the total composition; a humectant in an amount between about 1% and about 20% by weight of the total composition; and a preservative in an amount between about 0.4% and about 0.8% by weight of the total composition.

8. The composition of claim 7, wherein said stabilizer system includes at least one stabilizer selected from the group consisting of magnesium aluminum silicate, xanthan gum, and sodium carboxy methyl cellulose.

9. The composition of claim 7, wherein said oil absorber is selected from the group consisting of bentonite, calcium silicate, magnesium silicate, talc, kaolin, zinc oxide, zinc stearate, magnesium carbonate, lithium stearate, oat flour and Fuller's earth.

10. The composition of claim 7, wherein said modifier is selected from the group consisting of:

$$CH_3(CH_2)_xCH_2OH$$

wherein x represents from 12 to 16.

11. The composition of claim 7, wherein said humectant is selected from the group consisting of glycerin, sorbitol, 1-3 butylene glycol, and propylene glycol.

12. A make-up composition including an oil-like material in an oil-in-water emulsion wherein said material forms an oil-like phase, the make-up composition including:
deionized water in an amount between about 20% and about 90% by weight of the total composition for forming an outer phase of the emulsion and a vehicle for additives;
a volatile silicone fluid in an amount between about 0.5% and about 20% by weight of the total composition for forming the oil-like phase, said silicone fluid being able to evaporate after application on a wearer so as to be able to yield an essentially oil-free film;
at least one oil absorber in an amount between about 0.5% to about 10% by weight of the total composition;
an emulsifier system in an amount between about 0.3% and about 17% of the total composition; and
a colorant which includes a pigment in an amount between about 1% and about 25% of the total composition,
wherein the composition is viscous with a viscosity between about 45,000 to about 150,000 centipoise so that the composition is a cream, lotion or ointment.

13. The make-up composition of claim 12, wherein said volatile silicone fluid is selected from the group consisting of hexamethyldisiloxane; 2,4,6,8-octamethylcyclotetrasiloxane; 2,4,6,8,10-decamethylcyclopentasiloxane; and 2,4,6,8,10,12-dodecamethylcyclohexasiloxane.

14. The make-up composition of claim 12, wherein said emulsifier system includes a first emulsifier and a second emulsifier.

15. The make-up composition of claim 14, wherein said first emulsifier is included in an amount between about 0.2% and about 15% by weight of the total composition and wherein said second emulsifier is included in an amount between about 0.1% and about 2% by weight of the total composition.

16. The make-up composition of claim 12 wherein said composition includes at least one additive selected from the group consisting of a stabilizer system, feel and texture modifiers, dispersants and humectants.

17. The make-up composition of claim 16, wherein said composition includes at least one stabilizer in an amount between about 0.2% and about 4.5% by weight; at least one modifier in an amount between about 0.2% and about 10% by weight; at least one dispersant in an amount between about 0.25% and about 5.75% by weight; and at least one humectant in an amount between about 1% and about 20% by weight.

18. The make-up composition of claim 12, wherein said colorant is selected from a group consisting of iron oxide, titanium dioxide and zinc oxide.

19. The make-up composition of claim 17, wherein said dispersant is selected from the group consisting of acetylated ester of ethoxylated ether of lanolin alcohol and the sodium salt of polymethacrylic acid.

20. A therapeutic oil-in-water emulsion composition free of animal, vegetable and mineral oils, the composition including, by weight of the total composition,:
water in an amount between about 20% and about 90%;
at least one emulsifier in an amount between about 0.3% and about 17%;
an anti-acne agent in an amount between about 1% and about 10%;
at least one oil absorber in an amount up to about 10%; and
a volatile silicone fluid in an amount between about 0.5% to about 20%, said fluid being able to evaporate after application on wearer at normal body temperature so as to impart an essentially oil-free composition on said wearer after evaporation thereof,
wherein said composition is viscous with a viscosity between about 45,000 to about 150,000 centipoise so that the composition is a cream, lotion or ointment.

21. The therapeutic composition of claim 20, wherein said volatile silicone fluid is selected from the group consisting of hexamethyldisiloxane; 2,4,6,8-octamethylcyclotetrasiloxane; 2,4,6,8,10-decamethylcyclopentasiloxane; and 2,4,6,8,10,12-dodecamethylcyclohexasiloxane and is included in said composition in an amount between about 5% and about 20% by weight of the total composition.

22. The therapeutic composition of claim 20, wherein said anti-acne agent is selected from the group consisting of sulfur and benzoyl peroxide and is included in an amount between about 2.5% and about 10% by weight of the total composition.

23. The therapeutic composition of claim 20, wherein said composition includes a first emulsifier in an amount between about 0.2% and about 15% by weight of the total composition and a second emulsifier in an amount between about 0.1% and about 2% by weight of the total composition and wherein said first emulsifier is a polyoxyethylene alkane ether and wherein said second emulsifier is ethoxylated cholesterol.

* * * * *